US006440726B1

(12) United States Patent
Resnick (10) Patent No.: US 6,440,726 B1
(45) Date of Patent: Aug. 27, 2002

(54) EXPRESSION VECTORS COMPRISING MULTIPLE SHEAR STRESS RESPONSIVE ELEMENTS (SSRE) AND METHODS OF USE FOR TREATING DISORDERS RELATED TO VASCULOGENESIS AND/OR ANGIOGENESIS IN A SHEAR STRESS ENVIRONMENT

(75) Inventor: Nitzan Resnick, Haifa (IL)

(73) Assignee: Florence Medical, Ltd., Kfar Saba (IL)

( * ) Notice: Subject to any disclaimer, the term of this patent is extended or adjusted under 35 U.S.C. 154(b) by 0 days.

(21) Appl. No.: 09/220,510

(22) Filed: Dec. 24, 1998

(51) Int. Cl.$^7$ ........................... C12N 15/63; C12N 15/00

(52) U.S. Cl. ................... 435/320.1; 435/69.1; 435/455; 435/325; 514/44

(58) Field of Search ............................. 435/320.1, 325, 435/69.1, 455; 514/44; 429/43.2

(56) References Cited

U.S. PATENT DOCUMENTS 5,834,248 A 11/1998 Falb
5,834,306 A 11/1998 Webster et al.

OTHER PUBLICATIONS

Anderson et al., Human gene therapy, Apr. 30, 1998, Nature, p. 25–30.*
Verma et al., Gene therapy–promise, problems and prospects, Sep. 18, 19997, Nature, vol. 389, pp. 239–242.*
Abdo MD et al., Flow–dependent Regulation of Gene Expression in Vascular Endothelial Cells, Oct. 30, 1995, p. 19–32.*
Malek, A. et al. "Physiological Fluid Shear Stress Causes Downregulation of Endothelin–1 mRNA in Bovine Aortic Endothelium", The American Physiological Society, 1992, pp. C389–C396.
Ohno, M. et al. "Fluid Shear Stress Induces Endothelial Transforming Growth Factor Beta–1 Transcription and Production", Modulation by Potassium Channel Blockade. J. Clin. Invest. The American Society For Clinical Investigation, Inc. vol. 95, Mar. 1995, 1363–1369. pp. 1363–1369.
Morigi, M. et al. "Fluid Shear Stress Modulates Surface Expression of Adhesion Molecules by Endothelial Cells". 1995 by The American Society of Hematology. Blood, vol. 85, No. 7 (Apr. 1), 1995: pp 1696–1703.
Hsieh, HJ. et al. "Pulsatile and Steady Flow Induces c–fos Expression in Human Endothelial Cells". 1993 Wiley–Liss, Inc. Journal of Cellular Physiology 154–143–151 (1993).
Ando, J. et al. "Down–Regulation of Vascular Adhesion Molecule–1 by Fuid Shear Stress in Cultured Mouse Endothelial Cells", Annals New York Academy of Sciences, pp. 148–156.

Khachigian, L. et al. "Egr–1 is Activated in Endothelial Cells Exposed to Fluid Shear Stress and Interacts With a Novel Shear–Stress–Response Element in the PDGF A–Chain Promoter", Arteriosclerosis, Thrombosis, and Vascular Biology vol. 17, No. 10 Oct. 1997, 1997 American Heart Association, Inc., pp. 2280–2286.

Ohno, M. et al. "Shear Stress Elevates Endothelial cGMP", Circulation vol. 88, No. 1 Jul. 1993, pges 193–197.

Malek, A. et al. "Regulation of Endothelin 1 gene by Fluid Shear Stress is Transcriptionally Mediated and Independent of Protein Kinase C and cAMP". Proc. Natl. Acad. Sci. USA vol. 90, pp. 5999–6003, Jul. 1993 Cell Biology.

Malek, A. et al. "Fluid Shear Stress Differentially Modulates Expression of Genes Encoding Basic Fibroblast Growth Factor and Platelet–derived Growth Factor B Chain in Vascular Endothelium", J. Clin. Invest The American Society for Clinical Investigation, Inc. vol. 92, Oct. 1993, 2013–2021.

Takahashi, et al. M. "Mitogen–activated Protein Kinase (ERK1/2) Activation by Shear Stress and Adhesion in Endothelial Cells", Essential Role for a Herbimycin–sensitive Kinase. J. Clin. Invest. The American Society for Clinical Investigation, Inc. Volum 98, No. 11, Dec. 1996, 2623–2631.

Schwachtgen, J–L. et al. "Fluid Shear Stress Activation of egr–1 Transcription in Cultured Human Endothelial and Epithelial Cells Is Mediated via the Extracellular Signal–related Kinase 1/2 Mitogen–activateed Protein Kinase Pathway", J. Clin. Invest. The American Society for Clinical Investigation, Inc. vol. 101, No. 11, Jun. 1998, 2540–2549.

Jalali, S. et al. "Shear Stress Activates p60src–Ras–MAPK Signaling Pathways in Vascular Endothelial Cells". 1998 American Heart Association, Inc. pp. 117–234.

Ando, J. et al. "Flow–dependent Regulation of Gene Expression in Vascular Endothelial Cells". Japanese Heart Journal, Jan. 1996, vol. 37, No. 1, pp. 19–32.

Shyy, J. et al. "The cis–acting phorbol ester "12–O–tetradecanoylphorbol 13–acetate"–Responsive Element is Involved in Shear Stress–induced Monocyte Chemotactic Protein 1 Gene Expression". Proc. Natl. Acad. Sci, USA, vol. 92, pp. 8069–8073, Aug. 1995 Medical Sciences.

(List continued on next page.)

Primary Examiner—Dave T. Nguyen
(74) Attorney, Agent, or Firm—Nath & Associates PLLC; Harold L. Novick; Todd L. Juneau (57) ABSTRACT

This invention provides expression vectors comprising multiple shear stress responsive elements and methods of treating disorders related to or associated with vasculogenesis and/or angiogenesis in the vasculature.

19 Claims, 1 Drawing Sheet

OTHER PUBLICATIONS

Khachigian, L. et al. "Nuclear Factor–kB Interacts Functionally With The Platelet–Derived Growth Factor B–Chain Shear–Stress Response Element in Vascular Endothelial Cells Exposed to Fluid Shear Stress". J. Clin. Invest. the American Society For Clinical Investigation, Inc. vol. 96, Aug. 1995, 1169–1175.

Resnick, N. et al. "Platelet–Derived Growth Factor B Chain Promoter Contains A Cis–acting Fluid Shear–Stress–Responsive Element". Proc. Natl. Acad. Sci. USA 90 (1993), pp. 4591–4595.

Bussolari, S. et al. "Apparatus for Subjecting Living Cells to Fluid Shear Stress". Rev. Sci. Instrum. 53(12), Dec. 1982, 1982 American Institute of Physics, pp. 1851–1854.

Sideman, S. et al. "Analytical and Quantitative Cardiology", Analytical and Quantitative Cardiology. Pp. 155–164.

Resnick, N. et al. "Endothelial Gene Regulation by Laminar Shear Stress". Analytical and Quantitative Cardiology, Chapter 13. Pp. 155–164.

Nagel, T. et al. "Shear Stress Selectively Upregulates Intercellular Adhesion Molecule–1 Expression In Cultured Human Vascular Endothelial Cells", J. Clin. Invest. The American Society for Clinical Investigation, Inc. vol. 94, Aug. 1994, 885–891.

Malek, A. et al. "Control Of Endothelial Cell Gene Expression By Flow", J. Biomechanics, vol. 28, No. 12, pp. 1515–1528, 1995, 1995 Elsevier Science Ltd.

Sumpio, B. et al. Regulation of tPA in Endothelial Cells Exposed to Cyclic Strain: role of CRE, AP–2, and SSRE binding sites. 1997 The American Physiological Society. Pp. C1441–C1448.

Resnick, N. et al. "Hemodynamic Forces are Complex Regulators of Endothelial Gene Expression", The FASEB Journal, vol. 9, Jul. 1995. Pp. 874–882.

Sumpio, B. et al. "Regulation of PDGF–B in Endothelial Cells Exposed to Cyclic Strain", 1998 American Heart Association, Inc. Pp. 349–355.

* cited by examiner

FIG.1

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial sequence
<220> FEATURE:
<223> OTHER INFORMATION: Description of Artificial sequence:
      A PDGF-A Shear Stress Response Element.

<400> SEQUENCE: 1
gggggcgggg gcggggg                                                      17

<210> SEQ ID NO 2
<211> LENGTH: 6
<212> TYPE: DNA
<213> ORGANISM: Artificial sequence
<220> FEATURE:
<223> OTHER INFORMATION: Description of Artificial sequence:
      A PDGF-B Shear Stress Response Element.

<400> SEQUENCE: 2 gagacc                                                                   6

<210> SEQ ID NO 3
<211> LENGTH: 7
<212> TYPE: DNA
<213> ORGANISM: Artificial sequence
<220> FEATURE:
<223> OTHER INFORMATION: Description of Artificial sequence:
      a TRE Shear Stress Response Element.

<400> SEQUENCE: 3 tgactcc                                                                  7

<210> SEQ ID NO 4
<211> LENGTH: 11
<212> TYPE: DNA
<213> ORGANISM: Artificial sequence
<220> FEATURE:
<223> OTHER INFORMATION: Description of Artificial sequence: An SP1
      sequence.
```

-continued

```
<400> SEQUENCE: 4
ggggcgggcg g                                                                11

<210> SEQ ID NO 5
<211> LENGTH: 85
<212> TYPE: DNA
<213> ORGANISM: Artificial sequence
<220> FEATURE:
<223> OTHER INFORMATION: Description of Artificial sequence: Specific
      vector sequence

<400> SEQUENCE: 5
cgcctgagac ccccggggcg gggcggagac cccctgactc cccactctgg gggcccgcc           60 ccgcctctgg gggactgagg gagct                                                85

<210> SEQ ID NO 6
<211> LENGTH: 78
<212> TYPE: DNA
<213> ORGANISM: Artificial sequence
<220> FEATURE:
<223> OTHER INFORMATION: Description of Artificial sequence: Specific
      vector sequence

<400> SEQUENCE: 6 tcgaggggggg cggggggcggg ggtgactccg agacccccac cccccgcccc cgcccccact        60
gtggctctgg gggtctag                                                        78
```

EXPRESSION VECTORS COMPRISING MULTIPLE SHEAR STRESS RESPONSIVE ELEMENTS (SSRE) AND METHODS OF USE FOR TREATING DISORDERS RELATED TO VASCULOGENESIS AND/OR ANGIOGENESIS IN A SHEAR STRESS ENVIRONMENT

FIELD OF INVENTION

This invention provides expression vectors comprising multiple shear stress responsive elements and gene therapy methods for treating disorders related to or associated with vasculogenesis and/or angiogenesis by introducing the vectors in the vasculature having hemodynamic forces such as fluid shear stress forces. Further, this invention provides methods to monitor shear stress activities, to screen and select for target genes and methods of identifying and describing genes which are differentially expressed in cardiovascular disease states, relative to their expression in normal, or non-cardiovascular disease states. Lastly, this invention provides methods for the diagnostic monitoring of patients undergoing clinical evaluation for the treatment of cardiovascular disease and for the identification, monitoring and therapeutic use of compounds as treatments of cardiovascular disease.

BACKGROUND OF THE INVENTION

The construction of blood vessels consists of two processes: vasculogenesis, the establishment of vascular network during embryogenesis from multipotential mesanchymal progenitors, and angiogenesis, the sprouting of existing blood vessels which occurs both in the embryo and in the adult (1–5). Endothelial cells are the major players in both processes, they migrate and proliferate and than assemble into tubes with tight cell-cell connections. Peri-endothelial cells are recruited to support the endothelial tube, providing maintenance and modulatory functions to the vessel. These cells are perycytes in the capillaries, smooth muscle cells in larger vessels and cardiac mycocytes in the heart.

The establishment and remodeling of blood vessels is controlled by paracrine signals, many of which are protein ligands that bind to modulate the activity of transmembrane tyrosine kinase receptors (1,3,6). Among these molecules are Vascular Endothelial Growth factor (VEGF) and its receptors, Angiopeitin 1 and 2 and their receptor (Tie 1 and 2), Basic Fibroblast Growth Factor (bFGF), Platelet derived Growth factor (PDGF), and Transforming Growth Factor (TGF). Recently, some of these molecules have been disrupted in the embryo (null-mice), or mutated in the adult. The animal models pointed to a certain order in the formation of the blood vessel, and further stressed the role of the endothelium in all stages of vessel formation. The dominant role of VEGF and its receptors in preliminary stages of angiogenesis and vasculogenesis has been demonstrated in null animals which die in early stages of embryogenesis even in heterozygous animals (7–9). Null animals lacking the Flk1 receptor had no endothelial cells, while null animals lacking the Flt1 receptor failed to form tubes. When the Tie2 receptor or its ligands angiopoietin 1 and 2 were disrupted (10–14), endothelial cells organized into a tube shape, but failed to recruit the periendothelial cells. Interestingly, similar phenotypes were observed in animals null in PDGF-B, TGF- and tissue factor (15–18) suggesting that the binding of angiopoietin to its receptor may lead to the secretion of these molecules from the endothelium, pointing again for the role of these cells in the various steps of vessel formation.

The scheme evolving suggests that the binding of VEGF to its receptors, plays an important role in the primary steps of vessel formation, differentiation, migration and proliferation of endothelial cells and the formation of the primary tube, while the binding of Angiopoietin1 to its Tie2 receptor mediate the maturation of the vessel, recruitment of peri-endothelial supporting cells and maintenance of vessel integrity and quiescence. These same molecules play an additional role in loosening the interaction of the endothelium with its matrix and support cells, enabling the sprouting of new vessels (6). Recently it was suggested that the binding of Angiopoietin 2 to Tie2 plays a role in regression of already existing vessels (6,13).

In mature blood vessels, endothelial cells, by virtue of their unique anatomical position, are constantly exposed to the fluid mechanical forces generated by the flowing blood (See, William R. Milnor in Chapter 6 entitled "The Normal Hemodynamic State" of the book entitled "Hemodynamics", published by Williams & Wilkins, Maryland (1989) and U.S. Pat. Nos. 5,199,298, 5,052,228 and 4,926,696 for measuring shear stress. These hemodynamic forces, which include hydrostatic pressure, cyclic strain and frictional wall shear stress, constitute a special category of physical stimuli that, in addition to better characterized biochemical stimuli, can elicit important biological responses in the cells that compose the blood vessel wall (23). The non-random distribution of early atherosclerotic lesions observed both in natural disease processes in human and in experimental animal model has long been cited as suggestive evidence for the role these forces play in the pathogenesis of cardiovascular diseases (24,25). Both in-vivo studies and in-vitro experiments, using well defined model flow systems, have demonstrated that wall shear stresses can modulate various aspects of endothelial structure and function, changes that are mediated via up or down regulation of endothelial gene expression at the transcription level (26,27).

Hemodynamic forces and more specifically, fluid shear stress, regulate the expression of PDGF and TGF( (26,27). The activity of extracellular degrading enzymes and the levels of their transcripts are all induced in endothelial cells exposed to flow (23,27). Recently, it was demonstrated that NO is a down stream signaling molecule in angiogenesis induced by VEGF, but not FGF (35). Endothelial NO synthase is highly regulated in cells exposed to shear stress.

One of the intriguing and unanswered questions is the role that hemodynamic forces play in the formation and maturation of blood vessels in both vasculogenesis and angiogenesis. The role of these forces in vessel formation has been so far only suggestive (4,5). The formation of coronary collaterals was suggested to be affected by hypoxia. Although VEGF and its receptors, as well as PDGF-B, are all induced in hypoxic endothelial cells and myocytes in-vitro (29–32), several in-vivo models demonstrated that collateral growth occurs outside the hypoxic area. In the canine model collateral growth occurs in the epicardium (which is not hypoxic) and proceeds at the time when even the endocardium is not hypoxic anymore (33). Another example from the peripheral circulation, is the ischemic foot (as a result of femoral artery occlusion) where collaterals develop in both ischemic and more distant non-ischemic regions (34). During maturation of the vessel changes in the composition of the extracellular matrix occur, and tight junctions are formed (19,20). Are these changes stimulated by the flow of blood in the newly formed vessel? Furthermore, angiogenesis often involves massive sprouting of the already existing vessels, which is accompanied by the regression of some of the newly formed tubes (21,22). Is this balance (formation versus regression) affected by changes in the rate and pattern of blood flow through these newly formed tubes? Do changes in the pattern and magnitude of hemodynamic forces in big vessels affect the formation of smaller vessels (vasa vasorum) in the adventitia (37)? Answers to these questions are essential for better understanding the multiple steps of vasculogenesis and angiogenesis.

SUMMARY OF THE INVENTION

This invention provides expression vectors comprising multiple shear stress responsive elements. Also this invention provides gene therapy methods for treating disorders related to or associated with vasculogenesis and/or angiogenesis by introducing the vectors described herein in the vasculature having hemodynamic forces such as fluid shear stress forces. Hemodynamic forces, which include hydrostatic pressure, cyclic strain, and frictional wall shear stress, play an important role in the formation and maturation of blood vessels by regulating endothelial genes through Shear Stress Responsive Elements (SSRE) in promoters of endothelial shear stress responsive genes.

This invention provides a recombinant vector comprising a multiple number of nucleic acids of Shear Stress Response Elements (SSRE). The Shear Stress Response Elements (SSRE) are nucleic acid sequences from promoters of growth factors, thrombogenic factors or angiogenic genes.

This invention provides a pharmaceutical composition comprising the vector comprising a multiple number of nucleic acids of Shear Stress Response Elements (SSRE) and a suitable diluent or carrier.

This invention provides a method of stimulating endothelial cell proliferation comprising introducing/transfecting the endothelial cells with an effective amount of the vector comprising a multiple number of nucleic acids of Shear Stress Response Elements (SSRE) and a suitable diluent or carrier wherein the Shear Stress Response Elements transcriptionally regulate endothelial cell gene expression, thereby stimulating endothelial cell proliferation. As contemplated herein, endothelial cells are vascular endothelial cells or capillary endothelial cells.

This invention provides a method of modulating vascular permeability in a mammal, comprising administering to said mammal an effective amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby modulating vascular permeability in the mammal.

This invention provides a method of stimulating the formation, maturation or regression of blood vessels of a subject, comprising administering to said subject an effective amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby stimulating the formation, maturation or regression of blood vessels.

This invention provides a method of modulating genes or proteins involved in vascular diseases which comprises administering to a subject with the vascular disease an effective amount of the pharmaceutical composition comprising the vector comprising a multiple number of nucleic acids of Shear Stress Response Elements (SSRE) and a suitable diluent or carrier, wherein the pharmaceutical composition is administered to the subject in the vasculature with the proviso that the vasculature has shear stress forces, so as to permit the Shear Stress Response Elements to be activated by the shear stress and transcriptionally regulate endothelial cell gene expression, thereby modulating genes or proteins involved in the vascular diseases.

This invention provides a method of treating a subject having a vasculogenic and/or angiogenic disorder comprising administering to the subject an amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby treating the subject having the vasculogenesis and/or angiogenesis disorder.

The present invention relates to a method for revascularization of ischemic tissues, development of collateral vessels and improvement of function in peripheral and myocardial ischemic tissue and enhancing the level of perfusion of blood to a target tissue. Also, the present invention relates to a method for treating a target tissue suffering from or at risk of suffering from ischemic damage, and a method of inducing angiogenesis in a target tissue.

This invention provides a method for screening test compounds for the ability to regulate endothelial cell expression or angiogenesis and/or vasculogenesis comprising: (a) contacting a endothelial cells with the compound to be tested; (b) determining the amount or expression of the endothelial cells or the amount of angiogenesis and/or vasculogenesis produced as a result of the test compound; (c) stimulating endothelial cells by introduction of the vector provided herein; (d) determining the amount or expression of the endothelial cells or the amount of angiogenesis and/or vasculogenesis produced as a result of the vector; (e) comparing the amount of angiogenesis and/or vasculogenesis produced as a result step (b) to that of step (d), wherein an increased amount of expression of the endothelial cells or the amount of angiogenesis and/or vasculogenesis of the test compound means that the test compound regulates endothelial cell expression angiogenesis and/or vasculogenesis.

This invention provides methods to monitor shear stress activities, to screen and select for target genes and methods of identifying and describing genes which are differentially expressed in cardiovascular disease states, relative to their expression in normal, or non-cardiovascular disease states and a method for the identification and therapeutic use of compounds as treatments of cardiovascular disease. Lastly, this invention provides methods for the diagnostic monitoring of patients undergoing clinical evaluation for the treatment of cardiovascular disease, and for monitoring the efficacy of compounds in clinical trials.

DETAILED DESCRIPTION OF FIGURES

DETAILED DESCRIPTION OF THE INVENTION

The formation of blood vessels via vasculogenesis, formation of blood vessels from newly differentiated mesanchymal progenitors, and angiogenesis, the sprouting of already existing blood vessels, accompanies many physiological and pathological processes during embryogenesis and adulthood. The major players in these two processes are endothelial cells, which differentiate, proliferate, migrate and assemble into new tubes.

The endothelium also recruit the peri-endothelial cells which support the tube and contribute to its unique remodeling capability. After the assembly of the endothelium into tubes, blood starts to flow through the newly formed vessels, a step which is followed by the maturation of the vessel, formation of tight junctions and changes in the composition of the extracellular matrix, but is also accompanied by the regression of some of these newly formed vessels. The nature of the relationship between hemodynamic forces generated by the flowing blood and vessel maturation has never been tested. Fluid shear stress transcriptionally regulates endothelial gene expression, a process which is mediated by shear stress responsive promoter elements. Several novel shear stress response elements have been defined herein, that bind endothelial cells transcription factors which are activated by shear stress forces.

Fluid shear stress by regulating the expression of endothelial genes, through shear stress response promoter elements, plays an important role in the formation, and maturation of blood vessels. As such, "synthetic" shear stress responsive promoters have been constructed containing positive SSREs which have been tested under various in-vitro shear stress regimes and patterns. Shear stress includes pulsatile, turbulent, oscillatory, disturbed LSS, shear stress gradients.

This invention provides expression vectors comprising multiple shear stress responsive elements and methods of use for treating disorders related to or associated with vasculogenesisis and/or angiogenesis in the vasculature which has shear stress forces. Mechanical forces, as shear stress, are important modulators of cellular functions in many tissues and particular important in the cardiovascular system to maintain homeostasis of blood vessels. During physiological condition shear flow stress is a laminar steady state force, different than those acting at the branch points of the blood vessels. In pathological events, complex shear stresses are involved in the development of cardiovascular diseases such as atherosclerosis and hypertension. Development of such pathologies are thought to be initiated by function/dysfunction of vascular endothelial cells. The vascular endothelium constitutes the interface between the blood and the vessel wall, as such, it is exposed to mechanical forces produced by the arterial pressure variations during the cardiac cycle, and i.e., the blood flow induced wall shear stress and the circumferential cyclic stretch of the whole vessel wall. Blood flow interaction with the vascular endothelium represent a specialized example of mechanical regulation of cell function that has important physiological and pathological consequences. Blood flow plays an important role in the morphogenesis of blood vessels, for instance increase in blood flow induces dilation of the blood vessels while decrease in blood flow cause reduction in blood vessel diameter.

The remodeling of blood vessels accompanies physiological and pathological processes such as, angiogenesis and vasculogensis, atherosclerosis, hypertension and restenosis. Vessel remodeling occurs in response to both biochemical and biomechanical stimuli, and has been shown to be dependant on the presence of an intact endothelial layer. By virtue of their anatomical position, endothelial cells are constantly exposed to hemodynamic forces generated by the flowing blood, forces that consist of fluid shear stress, cyclic strain and pressure. These forces affect endothelial cells structure and function, changes that are often mediated by the induction or shut-off of endothelial genes.

This invention provides a recombinant vector comprising a multiple number of nucleic acids of Shear Stress Response Elements (SSRE). In one embodiment the Shear Stress Response Elements (SSRE) are from promoters of growth factors, thrombogenic factors or angiogenic genes. In one embodiment the nucleic acids are in a sense orientation. In another embodiment the nucleic acids are in a sense or an anti-sense orientation. Each of the nucleic acids may be in a 5' to 3' direction in the vector or may be in a 3' to 5' direction in the vector.

As defined herein "Shear Stress Response Element" means a nucleic acid from the promoter of genes which regulates endothelial genes through shear stress forces. The gene may encode for growth factors, thrombogenic factors or angiogenic genes. A SSRE is a promoter element necessary and sufficient to induce (or suppress) gene expression in endothelial cells exposed to shear stress.

It is contemplated by this invention that the vector comprises a single nucleic acid of the SSRE or multiple SSREs. For example, in one embodiment the vector comprises the Shear Stress Response Element PDGF-A. In another embodiment the vector comprises the Shear Stress Response Element PDGF-B. In another embodiment the vector comprises the Shear Stress Response Element TRE. In another embodiment the vector comprises the Shear Stress Response Element SP 1. In another embodiment the vector comprises the Shear Stress Response Element PDGF-A and the Shear Stress Response Element PDGF-B. In another embodiment the vector comprises the Shear Stress Response Element PDGF-A and the Shear Stress Response Element TRE. In another embodiment the vector comprises the Shear Stress Response Element PDGF-B and the Shear Stress Response Element TRE. In another embodiment the vector comprises the Shear Stress Response Element PDGF-A and the Shear Stress Response Element SP1. In another embodiment the vector comprises the Shear Stress Response Element PDGF-B and the Shear Stress Response Element SP1.

In the preferred embodiment the vector comprises multiple number of SSREs. In one embodiment the vector comprises the Shear Stress Response Element are Shear Stress Response Element PDGF-B, Shear Stress Response Element PDGF-B, Shear Stress Response Element SP1, and Shear Stress Response Element TRE. In another embodiment the Shear Stress Response Element are Shear Stress Response Element PDGF-A, Shear Stress Response Element PDGF-B, Shear Stress Response Element TRE As defined herein "PDGF-A" means a Platelet Derived Growth Factor- A which has the nucleic acid sequence as follows: GGGGGCGGGGGCGGGGG (SEQ ID NO. 1). As defined herein "PDGF-B" means a Platelet Derived Growth Factor- B which has the nucleic acid sequence as follows:

GAGACC (SEQ ID NO. 2). As defined herein "TRE" means a nucleic acid which has the following sequence TGACTCC (SEQ ID NO. 3). As defined herein SP 1 means a nucleic acid which has the following sequence GGGGCGGGCGG (SEQ ID NO. 4).

In another embodiment the vector comprises the following nucleic acid sequence CGCCTGAGACCCC CGGGGGCGGGGCGGAGACCCCCTGACTCC CCACTCTGGGGGCCCCGCCCCGCCTCTGGGGGA CTGAGGGAGCT (SEQ ID NO 5). In another embodiment the vector comprises the following nucleic acid sequence TCGAGGGGGGCGGGGGCGGGGGTGACTCC GAGACCCCCACCCCCCGCCCCCGCCCCCACTGTGG CTCTGGGGGTCTAG (SEQ ID NO 6).

As contemplated herein, SSREs of the promoters from genes that are regulated by shear stress include but are not limited to: Human 15-lipoxygenase gene, Genebank Accession No. U88317 at position 3350..3355, Kritzik, M. R., Ziober, A. F., Sigal, E. and Conrad, D. J., Biochim. Biophys. Acta (1997); Protein Kinase, Genbank Accession No. 2992634, Donadelli, R., Benatti, L., Remuzzi, A., Morigi, M., Gullans, S. R., Benigni. A., Remuzzi, G. and Noris, M. Biochem. Biophys. Res. Commun. 246 (3), 881–887 (1998); FEG-1 gene which is expressed by vascular endothelial cells under shear stress., Genbank Accession No. E13350 and 3023539; Endothelin-converting enzyme (ECE-1) gene, Genbank Accession No. X91923 at position 233..238, Valdenaire, O, .J. Biol. Chem. 270 (50), 29794–29798 (1995); and Beta-tubulin folding cofactor D, Genbank Accession No. AJ006417; PGI synthetase; conexin43; c-myc; c-fos; c-jun; TGF-β; FGF; β -FGF; HO-1; Thrombomodulin; Thrombospondin; Laminin B 1; Mn/Cu/Zn SOD; ICAM-1; Endothlin-1; plasminogen activator 1; MADH dehydrogenase; acidic and basic fibroblast growth factors; vascular endothelial growth factors 1, 2, 3, A, B, C, and D; epidermal growth factor; transforming growth factors alpha and beta; tumor necrosis factor alpha; hepatocyte growth factor; vascular endothelium growth factor, EEGIR-3, FLT-1, VEGF, isoforms, variants, mimetics, alternate splices, fragments and mutants thereof) , placenta growth factor 1 and 2, endothelial pas domai protein-1, and insulin like growth factor. It is known by those skilled in the art how to localize element(s) within the promoter that are shear stress responsive. For example, one may employ 5'-nested deletion analysis. Using computer analysis and electromobility shift assays (EMSA) one is able to localize the shear stress responsiveness to an element within the region, and ligating the nucleic acid into a promoter construct and transfected into endothelial cells.

In another embodiment the vector further comprising a second nucleic acid or gene which encodes a peptide or protein. In one embodiment the second nucleic acid or gene which encodes a peptide or protein which is angiogenic. Angiogenic genes and proteins are known to those skilled in the art. In another embodiment the second nucleic acids encodes the following proteins or growth factors: NFkB, MCP-1, NFAT, sp1/Egr 1, c-fos, c-jun, c-myc, PDGF A, PDGF B, TM, b-FGF, TGF, eNOS, HO-1, cu/Zn SOD, VCAM-1, I-CAM, Connecxin 43, FLT-1, FLK-1, VCAM, PGI synthase, smad 6, smad 7, TGF-B, HB-EG CNP, COX-2, thrombospondin, ICAM, ELAM-1, cyclooxygenase, angiopeitin 1, tenscin, angiopeitin 2, laminin B1, IL- 1, I1–2, I1–3, I1–4, I1–4, IL-6,I1–7,I1–8, I1–9, I1–10, I1–11, I1–12, ACE, ICE, Vascular Endothelial Growth Factor (VEGF) Genbank Accession Nos: 2851617, 1718152, 137821, 3402014, 3402011, 3402013, 3402010, 3402008, 3402009, 3056721, 549320, and 451322, Placenta Growth Factor 1 and 2 (PLGF-1/PLGF-2) Genbank Accession No: 1709656, EPAS-1 Genbank Accession No:391429, EEGIR-3 Genbank Accession No. 1718189, FLT-1 Genbank Accession No. 125361, EDRF (Endothelin-Derived Relaxin Factor, hepatocyte growth factor/Scatter factor (HGF/SF), Platelet Derived Endothelial Cell Growth Factor (PD-ECGF), Urokinase Plasminogen Activator (uPA), or Cartillage Type II Collagen. It is contemplated that the vector comprises alleles, alternative-splicing products, analogs, fragments, isoenzymes, mimetics, mutants, synthetic forms or variants of the nucleic acid. Additional genes, proteins are in U.S. Pat. Nos. 5,332,671, 5,712,380, (Ferrara et al.), U.S. Pat. No. 5,240,848 (Keck et) and U.S. Pat. No. 5,219,739 (Tischer et al.), U.S. Pat. No. 5,338,840 (Bayne et al.) and U.S. Pat. No. 5,532,343 (Bayne et al.); International Patent Application WO in 5/24473 (Hu et al.) International Patent Application WO 98110071 PCT/LJS97/15471, European Patent Documents 476 983 (Bayne et al.), 506 477 (Bayne et al.), and 550 296 (Sudo et al.), and Japanese Patent Documents 1038100, 2117698, 2279698, and 3178996 which are incorporated by reference.

The angiogenic genes or proteins include natural and recombinant forms of a variety of peptides, e.g. growth factors and related molecules which are able to promote endothelial and smooth muscle cell proliferation leading to the formation of new blood vessels (angiogenesis).

In another embodiment the vector farther comprising a reporter gene. Reporter genes are known to those skilled in the art. For example, one may use, but is not limited to, the following reporter genes: luciferase, β-galactosidase, or β-lacatamase. Other reporter genes include but are not limited to: β-lactamase and other antibiotic resistant gene, a cell surface marker as MHC I or II sub-types, a receptor for growth factor or cell adhesion and any gene of interest for therapeutic reasons. Additionally, the vector may comprise a marker inserted may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein MRNA. These elements may include splice signals, as well as transcription promoters, enhancers, and termination signals. cDNA expression vectors incorporating such elements include those described by Okayama, Molec. CeIZ. Biol. 3:280(1983).

The transcribed gene under the SSRE transcription regulation (the reporter gene) can be also a gene that confirm resistant to a specific antibiotic as a selection marker in prokaryotes and eukaryotes cells (neomycin, tetracycline, kanamycine and other); The gene can be also a membrane protein as a screening marker (MHC I or II sub-type or other transmembrane protein as a receptor); The gene can be also encoding for a protein in an individual carrying a genetic defective gene product to be complement for therapeutic reasons. The gene can be also a secreted protein (enzymes or growth factors) that can be monitored by an external or internal biosensor. One attractive gene to be driven by SSRE is a gene encoding a secreted protein with an enzyme activity that can be monitored with a biosensor. This protein can be driven by the second unit of a bicistronic massage driven by SSRE to give low amount of gene products, however indicative of the SSRE activity. For in-vivo gene delivery, one can follow the activity of the second cistron to monitor on site (in-vivo) the first cistron. The second cistron include but not limited to lactate dehydrogenase, creatinase, esterase, alcohol dehydrogenase, all of which have characterized substrates and chemical reactions, and also enzymatic biosensor for such enzyme activities have been demonstrated in the art. A biosensor can be introduced in vivo to monitor SSRE activities for drug delivery or to be an indicative parameter of fluid shear stress. The SSRE vector could have one or more transcriptional units. For example, it can have an antibiotic selection marker and a Luciferase gene to monitor SSRE activity. The SSRE transcription unit can be monocistronic or bicistronic transcription unit, having IRES elements between the two genes.

Further, the SSRE vector can be used for selection of agonists and antagonists ligands, to shear stress signaling, from combinatorial peptide or antibody phage display libraries, for therapeutic means. Also, natural inhibitors or stimulators (from body fluids or other natural extracts) can be identified. In addition, this system can be used as an inducible system, to induce gene only when shear stress is applied. The methods described herein, provide functional screening (SSRE activity monitoring) and screening for target drug or target gene.

The Shear Stress Response Elements, include but are not limited to, RNA, cDNA, genomic DNA, fragments, isoenzymes, variants, mutants, alleles, synthetic forms, and mixed polymers, both sense and antisense strands, and may be chemically or biochemically modified or may contain non-natural or derivatized nucleotide bases, as will be readily appreciated by those skilled in the art so long as the SSRE retains its function, i.e. regulation of endothelial genes by shear stresses. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The nucleic acid may be modified. Such modifications include, for example. acetylation, carboxylation, phosphorylation, glycosylation, ubiquitination, labeling, e.g., with radionuclides, and various enzymatic modifications, as will be readily appreciated by those well skilled in the art. A variety of methods for labeling and of substituents or labels useful for such purposes are well known in the art, and include radioactive isotopes such as sup $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation.

Mutations can be made in SSRE such that a particular codon is changed to a codon which does not effect the functional/biologic properties of the SSRE, i.e. binding of transcriptional factors to specific DNA sequences within the SSRE. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

This invention provides screening for mutation within the SSRE sequences can be made to identify sequences with stronger SSRE activity as shear stress dependent transcription sequences, and also. The SSRE sequences may be screened for mutation, more potent binding proteins, as well for compounds that enhance or inhibit protein binding to SSRE for therapeutic means. Synthetic DNA sequences allow convenient construction of genes which will express analogs or "muteins". A general method for site-specific incorporation of unnatural amino acids into proteins is described in Noren, et al. *Science*, 244:182–188 (April 1989). This method may be used to create analogs with unnatural amino acids.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [RRL Press, (1986)]; B. Perbal, "A Practical Guide To Molecular Cloning" (1984).

A "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the MnRNA). A "recombinant DNA" is a DNA that has undergone a molecular biological manipulation.

The phrase "nucleic acid encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell. "Substantial identity" or "substantial sequence identity" mean that two sequences, when optimally aligned, such as by the programs GAP or BESTFIT using default gap which share at least 65–99 percent sequence identity, share at least 75 percent sequence identity, share at least 80 percent sequence identity, share at least 90 percent sequence identity, preferably at least 95 percent sequence identity, more preferably at least 99 percent sequence identity or more.

This invention provides for a replicable vector comprising the isolated nucleic acid molecule of the DNA virus. The vector includes, but is not limited to: a plasmid, cosmid, α phage or yeast artificial chromosome (YAC) which contains at least a portion of the isolated nucleic acid molecule. As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

Expression vectors which can be used other than adenovirus include, but are not limited to, the following vectors or their derivatives: human or animal viruses such as vaccinia virus, swinepox virus, pox virus, rhabdovirus, herpes simplex virus, baculovirus, herpes simplex virus, adeno-associated virus, retrovirus, cytomegalovirus, human cytomegalovirus, papillomavirus, Epstein Barr virus (EBV), mouse mammary tumor virus (MMTV), Moloney murine leukemia virus and plasmid and cosmid DNA vectors, to name but a few.

In one embodiment, the adenoviral vector is deficient in at least one essential gene function of the E1 region of the adenoviral genome, particularly the E1a region, more preferably, the vector is deficient in at least one essential gene function of the E1 region and part of the E3 region (e.g., an XbaI deletion of the E3 region) or, alternatively, the vector is deficient in at least one essential gene function of the E1 region and at least one essential gene function of the E4 region. Aadenoviral vectors deficient in at least one essential gene function of the E2a or E2b region and adenoviral vectors deficient in all of the E3 region also are contemplated here and are well known in the art. Furthermore, the viral vector's coat protein can be modified so as to incorporate a specific protein binding sequence.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general. Enhancers were originally detected as genetic elements that increased transcription from a promoter located at a distant position on the same molecule of DNA.

This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

Transcriptional and translational control sequences are DNA regulatory sequences, such as promoters, enhancers, polyadenylation signals, terminators, and the like, that provide for the expression of a coding sequence in a host cell. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgamo sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. A nucleic acid sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Below is a list of viral promoters, cellular enhancers and inducible enhancers that may be used, which include but are not limited to the following: ventricular myocyte specific promoter, cytomegalovirus, human cytomegalovirus, inflammatory promoters, TNF-α promoter, Rous Sarcoma Virus, Prostate Specific Antigen, Probasin, Immunoglobulin Heavy Chain, Immunoglobulin Light Chain, T-Cell Receptor, HLA DQ α and Dqβ, β-Interferon, Interleukin-2, Interleukin-2 Receptor, MHC Class II $5\alpha^{78}$. MHC Class II DRα, Actin, Muscle Creatine Kinase, Proalbumin (Transthyretin), Elastase I, Metallothionein, Collagenase, Albumin Gene, α-Fetoprotein, τ-Globin, c-fos, c-Ha-ras, Insulin, Neural Cell Adhesion Molecule (NCAM), α1-antirypole, 2B (TH2B) Histone, Muse or Type I Collagen, Glucose-Regulated Proteins (GRP94 and GRP78), Human Serum Amyloid A (SAA), Troponin I (TN I), Platelet-Derived Growth Factor, Duchenne Muscular Dystrophy, SV40, Polyoma, Retroviruses, Papilloma Virus, Hepatitis B Virus, or Gibbon Ape Leukemia Virus.

This invention provides a pharmaceutical composition comprising the vector comprising a multiple number of nucleic acids of Shear Stress Response Elements (SSRE) and a suitable diluent or carrier. In one embodiment the Shear Stress Response Elements (SSRE) are from promoters of growth factors, thrombogenic factors or angiogenic genes.

This invention provides a method of stimulating endothelial cell proliferation comprising transfecting the endothelial cells with an effective amount of the vector comprising a multiple number of nucleic acids of Shear Stress Response Elements (SSRE) and a suitable diluent or carrier wherein the Shear Stress Response Elements transcriptionally regulate endothelial cell gene expression, thereby stimulating endothelial cell proliferation. As contemplated herein, endothelial cells are vascular endothelial cells or capillary endothelial cells.

This invention provides a method of modulating vascular permeability in a mammal, comprising administering to said mammal an effective amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby modulating vascular permeability in the mammal.

This invention provides a method of stimulating the formation, maturation or regression of blood vessels of a subject, comprising administering to said subject an effective amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby stimulating the formation, maturation or regression of blood vessels.

This invention provides a method of modulating genes or proteins involved in vascular diseases which comprises administering to a subject with the vascular disease an effective amount of the pharmaceutical composition comprising the vector comprising a multiple number of nucleic acids of Shear Stress Response Elements (SSRE) and a suitable diluent or carrier, wherein the pharmaceutical composition is administered to the subject in the vasculature with the proviso that the vasculature has shear stress forces, so as to permit the Shear Stress Response Elements to be activated by the shear stress and transcriptionally regulate endothelial cell gene expression, thereby modulating genes or proteins involved in the vascular diseases.

This invention provides a method of treating a subject having a vasculogenic and/or angiogenic disorder comprising administering to the subject an amount of the pharmaceutical composition comprising the vector comprising a multiple number of nucleic acids of Shear Stress Response Elements (SSRE) and a suitable diluent or carrier, wherein the pharmaceutical composition is administered to the mammal in the vasculature with the proviso that the vasculature has shear stress forces, so as to permit the Shear Stress Response Elements to be activated by the shear stress and transcriptionally regulate endothelial cell gene expression, thereby treating the subject having the vasculogenesis and/or angiogenesis disorder.

Further, this invention provides further comprising administering to the subject an agent which acts as a vasoconstrictor, inflammatory agent, vasolidator, fibrinolytic activators, Tumor Necrosis Factor (TNF), or thrombotic factors.

Vasolidators are known to those skilled in the art. For example, the subject invention contemplates but are not limited to the following: prostacyclin, nitric oxide, natriuretic peptide or calcium antagonists. Vasoconstrictors are known to those skilled in the art. For example, the subject invention contemplates but are not limited to the following endothelin, thromboxan A2, angiotensin, kinins, kallikrein, and kininogen. Further, subject application incorporates in its entirety by reference the following: U.S. Pat. No. 5,594, 021, Thienyl-, furyl- and pyrrolyl sulfonamides and derivatives thereof that modulate the activity of endothelin; U.S. Pat. No. 5,691,344, Vasoconstrictive substituted dihydropyranopyridines; U.S. Pat. No. 5,441,95 1, Lipoxin compounds; U.S. Pat. No. 5,767,160, Method and formulation of stimulating nitric oxide synthesis; U.S. Pat. No. 5,824,682, Vasoconstrictive dihydrobenzopyran derivatives; U.S. Pat. No. 5,468,746, Compounds active on the cardiovascular system; and U.S. Pat. No. 5,733,916, Prevention and treatment of ischemia-reperfusion and endotoxin-related injury using adenosine and purino receptor antagonists.

Fibrinolytic activators are known to those skilled in the art. For example subject application incorporates in its entirety by reference the following: U.S. Pat. No. 4,873,083, Fibrinolytic composition; U.S. Pat. No. 5,316,766, Thrombosis treatment with fibrinolytics and prostacyclins; U.S. Pat. No. 4,996,050, Fibrinolytic activity enhancer; U.S. Pat. No. 4,600,580, Novel enzyme derivatives; U.S. Pat. No.

5,302,390, Hybrid proteins of human plasminogen and human t-PA, pharmaceutical compositions and methods of treatment; and U.S. Pat. No. 4,568,545, Thrombolytic agent; U.S. Pat. No. 5,106,741, Tissue plasminogen activator (TPA) analogs.

Thrombotic factors are known to those skilled in the art. For example subject invention application in its entirety by reference the following: U.S. Pat. No. 5,837,688, Use of thrombolytic reagents for prevention of vascular disease; U.S. Pat. No. 5,084,274, Inhibition of arterial thrombotic occlusion or thromboembolism; U.S. Pat. No. 5,509,896, Enhancement of thrombolysis with external ultrasound; U.S. Pat. No. 5,380,299, Thrombolytic treated intravascular medical device; U.S. Pat. No. 5,275,812, Method of treatment for myocardial infarction; U.S. Pat. No. 5,217,705, Method of diagnosing blood clots using fibrin-binding proteins; U.S. Pat. No. 5,637,299, Enhancement of thrombolytic therapy with deglycosylated forms of plasminogen; U.S. Pat. No. 5,643,915, Treatment of ischemia/reperfusion injury with thalidomide alone or in combination with other therapies; U.S. Pat. No. 5,021,044, Catheter for even distribution of therapeutic fluids; U.S. Pat. No. 4,582,854, 7-oxabicycloheptane substituted oxa prostaglandin analogs useful in the treatment of thrombolytic disease.

Vasculogenic and/or angiogenic disorders are known to those skilled in the art. For examples the disorders include but are not limited to: cardiovascular disorders, arteriosclerosis, Monckeebrg's arteriosclerosis, atherosclerosis, diabetic arteriosclerotic disease, hypertension, arterial hypertension, renovascular hypertension, myocardial ischemic disorders, coronary artery disease, angina pectoris, myocardial infarction, occlusive arterial disorders, peripheral atherosclerotic disease, thromboangitis obliterans, functional peripheral arterial disorders, cardiac arrythmias, bundle branch block, sick sinus syndrome, cardiomyopathy, hyperlipidemia, congestive heart failure, mitral stenosis, ischemi, reperfusion, shock, restenosis, arterial inflammation, retinovasculative disorders, mascular degeneration, diabetes, hypercholesterolemia, plaque formation, wound healing, lung or bladder disorders.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for person suffering with arthritis. Another pathological role associated with angiogenesis is found in atherosclerosis. U.S. Pat. No. 5,763,441, Compounds for the treatment of disorders related to vasculogenesis and/or angiogenesis; U.S. Pat. No. 5,763,198, Wound healing agents derived from platelets; and U.S. Pat. No. 5,376,636, Method for promoting tissue repair and regeneration are hereby incorporated by reference in their entirety.

The arterial tree which consists of large elastic and muscular vessels as well as arterioles and precapillaries vessels, is constantly exposed to hemodynamic forces varying widely in magnitude, frequency and direction. These forces consist of pressure acting perpendicular to the vessel wall, cyclic strain, and shear stress acting parallel to the wall, creating a frictional shear force on the surface of the endothelium. In large arteries the magnitude of shear stress is in the range of 10–40 dynes/cm$^2$, and it is over imposed with the pulsatile characteristic of the flow producing a range of shear stresses and shear stress gradients. In area of unique morphologies, such as curvatures and bifurcations, the steady laminar flow is disrupted to create regions of separated flow that include recirculation sites, which themselves may vary with the cardiac cycle. These secondary flows modify the profile of the original laminar flow therefore dictating the shear stress acting on the endothelium in these specific regions. Studies including in-vitro modeling systems, as well as, in-vivo measurements suggest that the values of shear stress in these regions vary from negative, to zero (in areas of flow separation) and up to positive values of 40 dynes/cm$^2$. Under non-physiological conditions (hypertension) these values are even higher. Thus, hemodynamic forces are important stimuli effecting the biology of the endothelium, which plays a pivotal role in both physiological processes and pathological conditions (atherosclerosis, hypertension, thrombosis).

In one embodiment the magnitude of shear stress is 1–50 dynes/cm$^2$. In another embodiment the magnitude of shear stress is 2–25 dynes/cm$^2$. In another embodiment the magnitude of shear stress is 10–25 dynes/cm$^2$. In another embodiment the magnitude of shear stress is 2–15 dynes/cm$^2$. In another embodiment of the method the magnitude of shear stress is 5–10 dynes/cm$^2$. In another embodiment of the method the magnitude of shear stress is 2–5 dynes/cm$^2$.

The vectors may be introduced into the desired host cells by methods known in the art, e.g., ex vivo viral vectors, particularly retroviral vectors, in vivo viral vectors, particularly defective viral vectors or adeno-associated virus vectors, transfection, electroporation, microinjection, transduction, cell fusion, DEAE dextran, calcium phosphate precipitation, lipofection (lysosome fusion), use of a gene gun, or a DNA vector transporter (see, e.g., U.S. Pat. No. 5,580,859, which is incorporated by reference and Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990). In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980, 289; Markowitz et al., 1988, J. Virol. 62:1120; Temin et al., U.S. Pat. No. 5,124,263; International Patent Publication No. WO 95/07358, published March 16, 1995, by Dougherty et al.; and Kuo et al., 1993, Blood 82:845. Retroviral vectors are especially attractive for transfecting solid tumors, since the cells of the tumor are replicating. Cell fusion (line 18) any cell fusion combination including but not limited to cell fusion between different cell type of different tissues origin, cell fusion between different species origin, cell fusion between mammalian and yeast or mammalian and prokaryote cell type. All these methods are known in the art as methods to transfer genetic materials. The vector may be introduced as a single vector or with a combination of other vectors, supplementing trans activity for the SSRE vector for enhances SSRE vector activities. For example. SSRE containing vector can be co-introduced with another vector that will introduce another genetic material to facilitate SSRE activities, to monitor transfection efficiency, to supply a missing component to the transfected cells (supplying helper function).

Alternatively, the vector can be introduced in vitro or in vivo by lipofection (lysosome fusion, including but not limited to cationic liposome, synthetic or natural lyposomes and neutral lyposomes). For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells, in this instance tumor cells, e.g., via tumor-specific cell surface receptors, represents one area of benefit. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector ex vivo or in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, U.S. Pat. No. 5,580,859, the contents of which are hereby incorporated by reference and e.g., Wu et al., 1992, J. Biol. Chem. 267:963–967; Wu and Wu, 1988, J. Biol. Chem. 263:14621–14624; Hartmut et al., Canadian Patent Application No. 2,012,311 , filed Mar. 15, 1990).

The present invention provides a method for the delivery of the vector to an arterial cell, blood vessel or vasculature by being carried by a microdelivery vehicle such as cationic liposomes and adenoviral vectors. DNA encoding different proteins may be used separately or simultaneously. Also, the arterial cell in an artery or blood vessel may be contacted via a balloon catheter coated with a hydrogel polymer. Other treatment methods include percutaneous transluminal angioplasty (PTCA), "Cutting balloon" angioplasty, directional coronary atherectomy (DCA), rotational coronary atherectomy (RCA), Ultrasonic breaking catheter angioplasty, transluminal extraction catheter (TEC) atherectomy, Rotablator atherectomy, and excimer laser angioplasty (ELCA). The vector described herein may be inserted by a single intra-femoral artery or intracoronary injection directly conducted deeply in the lumen of the one or both femoral or coronary arteries (or graft vessels) in an amount. U.S. Pat. No. 5,792,453 is hereby incorporated in its entirety.

In an approach which combines biological and physical gene transfer methods, plasmid DNA of any size is combined with a polylysine-conjugated antibody specific to the adenovirus hexon protein, and the resulting complex is bound to an adenovirus. vector. The trimolecular complex is then used to infect cells. The adenovirus vector permits efficient binding, internalization, and degradation of the endosome before the coupled DNA is damaged. Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992). Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type.

In another application the vector may be inserted/introduced by direct gene transfer of an expression vector. Alternatively, the vector by may implanted between the aorta and left ventricular myocardium. for induced site-directed neovascular development or administrating to the subject intrapericardial infusions. This provides exciting prospects for intervention in cardiac diseases in which myocardial oxygen supply is compromised and/or demand is increased. The induction of new collateral vessel formation should delay or halt the progression of coronary artery disease to myocardial infarction, as well as the advancement of ventricular hypertrophy to heart failure.

In yet another embodiment, the therapeutic compound can be delivered in a controlled release system into the vasculature. For example, the vector may be administered using intravenous injections, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Multiple applications provide an advantage over single applications in that they can be manipulated by such parameters as a specific geometry defined by the location on the target tissue where each application is administered.

The specific geometry of the multiple applications is defined by the location on the target tissue, either in two- or three-dimensional space, where each application of the ector is administered. The multiple applications preferably are spaced such that the points of application are separated by up to about 4 cm (e.g., about 0.5–4 cm), more preferably up to about 3 cm (e.g., about 1–3 cm), and most preferably up to about 2 cm (e.g., about 1–2 cm).

Preferably, a single application will be administered for about every 0.5–15 cm2 of the plane, more preferably for 15 about every 1–12 cm 2 of the plane, and most preferably for about every 1.5–7 cm 2 of the plane. The depth of the plane is preferably about 1–10 mm, more preferably about 2–7 mm, and most preferably about 3–5 mm. In three-dimensional space, a single application preferably is administered for up to about 50 cm (e.g., about 0.5–50 cm of target tissue, more preferably for up to about 35 cm (e.g., about 1–35 cm of target tissue, and most preferably for up to about 15 cm (e.g., about 3–15 cm) of target tissue. Furthermore, the multiple applications can define any suitable pattern or specific geometry.

In one embodiment, the vector or naked SSRE nucleic acid may be administered within a biocompatible polymer. Biocompatible polymers are known to those skilled in the art, see WO 97/16176, PCT/CA96/00725 which is incorporated by reference. In another embodiment, the vector or naked SSRE nucleic acid may preferably be implanted in the form of a disk, fibre or microsphere, with microsphere being the most preferred form. Preferably, the microsphere has a diameter no greater than about 500 m, more preferably no greater than about 200 pm, and most preferably from less than about 10 , UII to about 50 m. In another embodiment, the vector or naked SSRE nucleic acid is implanted into the peripheral ischemic tissue or in blood vessels close to the ischemic tissue to stimulate the growth of blood vessels or collaterals. In another embodiment, the vector or naked SSRE nucleic acid is incorporated into a wound care product applied to the surface of a wound such as a chronic wound or burn. Wound care products may be wet dressings, dry dressings, occlusive dressings, non-occlusivedressings, wound pastes, or any other product applied to a wound.

The disclosed microcapsules or microspheres which are any polymeric membrane that encloses an interior core of a different material, can be administered to a subject by various means, including implantation, injection, and infusion, via cannulas, catheters, pipette or directly through a needle from a syringe or using forceps or a trocar. When implanted into the subject the microcapsules and microspheres according to the present invention will become surrounded with well vascularized tissue.

Preferred biocompatible polymers for use in the present invention include polyacrylates, polyphosphazenes, various vinyl polymers including polyvinyl chloride, polyacrylonitrile, polyvinyl acetate, ethylene vinyl acetate, polyvinyl alcohol copolymers, polyvinyl amine copolymers, polyimides, polyether ketones, polysulphones, siloxanes, polyurethanes and polyamides, polycarbonates, polyesters and bioresorbables such as polyanhydrides, polyorthoesters, polycaprolactones, polyamino acids, polylactic/glycolic acid copolymers and polyhydroxybutyrates. More preferred biocompatible polymers are polyacrylates, with hydroxyethyl methacrylate-methyl methacrylate (HEMA-MMA) and hydroxyethyl methacrylate-methyl methacrylate-methacrylic acid (HEMA-MMA-MAA).

This invention provides administrating the vector or naked SSRE nucleic acid via intravascular catheters. Intravascular catheters and stents for delivery of drugs are known to those skilled in the art. For example, Patent Nos. 5,180,366; 5,171,217; 5,049,132; and 5,021,044; and PCT Publications WO 93/08866, WO 92/11895 and WO 97/123256 which are hereby incorporated by reference.

Tissues to be treated by the present invention will typically be adjacent to blood vessels, within the blood vessel, or more typically being adjacent to coronary and peripheral arteries, where the vector or naked SSRE nucleic acid is delivered transmurally within the adjacent blood vessel to promote angiogenesis from the delivery site within the blood vessel into the surrounding tissue. The target tissue will usually be ischemic, i.e., deprived of blood flow, but the present invention might also find use with promoting angiogenesis in non-ischemic tissues. The phrase "body lumen" will generally refer to blood vessels, including portions of the arterial vasculature and venous vasculature. Body lumen wall includes the neointimal, intimal, medial, adventitial and perivascular spaces, adjacent to the target site.

For example, delivery of the vector or naked SSRE nucleic acid according to the methods of the present invention could be performed after balloon angioplasty to enhance blood perfusion into ischemic tissue surrounding the treated stenotic region. Delivery of vector or naked SSRE nucleic acid could also be combined with delivery of other therapeutic agents intended for treating coronary artery disease, such as anti-5 thrombotic and fibrinolytic agents. Most commonly, balloon catheters having expandable distal ends capable of engaging the inner wall of a blood vessel and infusing an angiogenic factor directly therein are well-described in the patent literature. See, for example, U.S.Pat. Nos. 5,318,531; 5,304,121; 5,295,962; 5,286,254; 5,254,089; 5,213,576; 5,197,946; 5,087,244; 5,049,132; 5,021,044; 4,994,033; and 4,824,436 which are incorporated by reference.

Ultrasonically assisted drug delivery catheters (phonophoresis devices) are described in U.S. Pat. Nos. 15 5,362,309; 5,318,014; and 5,315,998. Other iontophoresis and phonophoresis drug delivery catheters are described in U.S. Pat. Nos. 5,304,120; 5,282,785; and 5,267,985. Finally, sleeve catheters having drug delivery lumens intended for use in combination with conventional angioplasty balloon catheters are described in U.S. Pat. Nos. 5,364,356 and 5,336,178.

It would also be possible to deliver the vector or naked SSRE nucleic acid by applying a thin layer of a hydrogel, glycosaminoglycans, or other polymeric carrier matrix to the endoluminal wall at the target location. Usually, the polymeric carrier will be biodegradable or bioeluting and serve as a temporary wall support while the vector or naked SSRE nucleic acid are released over time.

As can be readily appreciated by one of ordinary skill in the art, the methods and pharmaceutical compositions of the present invention are particularly suited to administration to a mammal, preferable a human subject.

As used herein, "pharmaceutical composition" could mean therapeutically effective amounts of the vector of the invention together with suitable diluents, preservatives, osolubilizers, emulsifiers, adjuvant and/or carriers. A "therapeutically effective amount"as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid. sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multi-lamellar vesicles, erythrocyte ghosts, or spheroplasts. Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, intratumorally, paracancerally, transmucosally, transdermally, intramuscularly, intravenously, intradermally, intravascularly, subcutaneously, intraperitonealy, intraventricularly, intracranially.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobial, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, California, p. 384). Often, a primary challenge with an antigen alone, in the absence of an adjuvant, will fail to elicit a humoral or cellular immune response. Adjuvant include, but are not limited to, complete Freud's adjuvant, incomplete Freud's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary nasal and oral. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutically acceptable form of the composition includes a pharmaceutically acceptable carrier. In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous. infusion sufficient to maintain concentrations of ten nanomolar to ten micromolar in the blood are contemplated.

This invention provides a method for screening test compounds for the ability to regulate endothelial cell expression or angiogenesis and/or vasculogenesis comprising: (a) contacting a endothelial cells with the compound to be tested; (b) determining the amount or expression of the endothelial cells or the amount of angiogenesis and/or vasculogenesis produced as a result of the test compound; (c) stimulating endothelial cells by introduction of the vector provided herein; (d) determining the amount or expression of the endothelial cells or the amount of angiogenesis and/or vasculogenesis produced as a result of the vector; (e) comparing the amount of angiogenesis and/or vasculogenesis produced as a result step (b) to that of step (d), wherein an increased amount of expression of the endothelial cells or the amount of angiogenesis and/or vasculogenesis of the test compound means that the test compound regulates endothelial cell expression angiogenesis and/or vasculogenesis. In one embodiment the test compounds are Shear Stress Response Elements, or promoter regions of angiogenic genes.

A "test composition", as used herein, is any composition such as a gene, SSRE, a nucleic acid sequence, a polypeptide, peptide fragment or composition created through the use of a combinatorial library or other combinatorial process that can be assayed for its ability to function in given capacity or compound which mimics the activity of the complex. Often such a test composition, nucleic acid sequence or polypeptide is, because of its sequence or structure, suspected of being able to function in a given capacity.

Any screening technique known in the art can be used to screen for regulators or modulators of angiogenesis and/or vasculogenesis. Identification and screening of antagonists or agonist is further facilitated by comparing the result of the test composition with the result of the vector described hereinabove. These techniques provide for the rational design or identification of agonists and antagonists. U.S. Pat. No. 5,165,938, Screening assays for compounds is incorporated in its entirety.

This invention provides methods to monitor shear stress activities, to screen and select for target genes, for gene therapy in other organs and methods of identifying and describing genes which are differentially expressed in cardiovascular disease states, relative to their expression in normal, or non-cardiovascular disease states and a method for the identification and therapeutic use of compounds as treatments of cardiovascular disease.

This invention provides methods for the diagnostic monitoring of patients undergoing clinical evaluation for the treatment of cardiovascular disease, and for monitoring the efficacy of compounds in clinical trials. Because the each of the SSRE of this invention are modulated, i.e up-regulated, treatment methods can be designed to enhance or increase their expression, particularly in endothelial cells. In addition, detecting expression of these genes in low amounts of normal expression provides for the diagnosis of cardiovascular disease.

This invention provides methods for the identification of genes which are involved in cardiovascular disease. Such genes may represent genes which are differentially expressed in cardiovascular disease conditions relative to their expression in normal, or non-cardiovascular disease conditions. Such differentially expressed genes may represent "target" and/or "fingerprint" genes. "Differential expression" as used herein refers to both quantitative as well as qualitative differences in the genes' temporal and/or tissue expression patterns. Thus, a differentially expressed gene may have its expression activated or completely inactivated in normal versus cardiovascular disease conditions, or under control versus experimental conditions. Such a qualitatively regulated gene will exhibit an expression pattern within a given tissue or cell type which is detectable in either control or cardiovascular disease subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, reverse transcriptase- (RT-) PCR and/or Northern analyses, which are well known to those of skill in the art.

Alternatively, a differentially expressed gene may have its expression modulated, i.e., quantitatively increased or decreased, in normal versus cardiovascular disease states, or under control versus experimental conditions. The degree to which expression differs in normal versus cardiovascular disease or control versus experimental states need only be large enough to be visualized via standard characterization techniques, such as, for example, the differential display technique described below. Other such standard characterization techniques by which expression differences may be visualized include but are not limited to quantitative RT-PCR and Northern analyses.

Differentially expressed genes may be further described as target genes and/or fingerprint genes. "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. A fingerprint gene may also have the characteristics of a target gene. "Target gene", as used herein, refers to a differentially expressed gene involved in cardiovascular disease in a manner by which modulation of the level of target gene expression or of target gene product activity may act to ameliorate symptoms of cardiovascular disease. A target gene may also have the characteristics of a fingerprint gene. A variety of methods may be utilized for the identification of genes which are involved in cardiovascular disease which are known to those skilled in the art.

For example, test cells. Cultured HUVEC monolayers are exposed to laminar sheer stress by rotating the culture in a specialized apparatus containing liquid culture medium, may also be compared to unrelated cells (e.g., fibroblasts) that are also treated with the compound, in order to screen out generic effects on gene expression that might not be related to the disease. Such generic effects might be manifest by changes in gene expression that are common to the test cells and the unrelated cells upon treatment with the compound.

In order to identify differentially expressed genes, RNA, either total or mRNA, may be isolated from one or more tissues of the subjects utilized in paradigms such as those described earlier in this Section. RNA samples are obtained from tissues of experimental subjects and from corresponding tissues of control subjects. Any RNA isolation technique which does not select against the isolation of mRNA may be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987–1993, Current Protocols in Molecular Biology, John Wiley & Sons, Inc. New York, both of which are incorporated herein by reference in their entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al.. 1984, Nature 308:149–153; Lee, S. W. et al., 1984, Proc. Natl. Acad. Sci. USA 88:2825), and, preferably, differential display (Liang, P., and Pardee, A. B., 1993, U.S. Pat. No. 5,262,311, which is incorporated herein by reference in its entirety), may be utilized to identify nucleic acid sequences derived from genes that are differentially expressed.

Subtractive hybridization techniques generally involve the isolation of mRNA taken from two different sources, e.g., control and experimental tissue, the hybridization of the MRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two MRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times. The pattern of clones resulting from the reverse transcription and amplification of the mRNA of two different cell types is displayed via sequencing gel electrophoresis and compared. Differences in the two banding patterns indicate potentially differentially expressed genes. Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis and/or RT-PCR.

Additionally, methods may be employed which result in the simultaneous identification of pathway genes which encode the protein interacting with a protein involved in cardiovascular disease. These methods include, for example, probing expression libraries with labeled protein known or suggested to be involved in cardiovascular disease, using this protein in a manner similar to the well known technique of antibody probing of lambda gt11 libraries.

Compounds identified via assays such as those described herein may be useful, for example, in elaborating the biological function of the target gene product, and for ameliorating cardiovascular disease. In instances whereby a cardiovascular disease condition results from an overall lower level of target gene expression and/or target gene product in a cell or tissue, compounds that interact with the target gene product may include compounds which accentuate or amplify the activity of the bound target gene protein.

In addition, animal-based cardiovascular disease systems, such as those described, may be used to identify compounds capable of ameliorating cardiovascular disease symptoms. Such animal models may be used as test substrates for the identification of drugs, pharmaceuticals, therapies, and interventions which may be effective in treating cardiovascular disease. For example, animal models may be exposed to a compound, suspected of exhibiting an ability to ameliorate cardiovascular disease symptoms, at a sufficient concentration and for a time sufficient to elicit such an amelioration of cardiovascular disease symptoms in the exposed animals. The response of the animals to the exposure may be monitored by assessing the reversal of disorders associated with cardiovascular disease, for example, by counting the number of atherosclerotic plaques and/or measuring their size before and after treatment. Antisense and ribozyme molecules which inhibit expression of the target gene may also be used in accordance with the invention to inhibit the aberrant target gene activity. Among the compounds which may exhibit the ability to ameliorate cardiovascular disease symptoms are antisense, ribozyme, and triple helix molecules.

The present invention provides a kit comprising the all the essential materials and reagents required for regulating angiogenesis and/or vasculogenesis. This generally will comprise selected expression constructs. Also included may be various media for replication of the expression constructs and host cells for such replication. Such kits will comprise distinct containers for each individual reagent. When the components of the kit are provided in one or more liquid solutions, the liquid solution preferably is an aqueous solution, with a sterile aqueous solution being particularly preferred. For in vivo use, the expression construct may be formulated into a pharmaceutically acceptable syringeable composition. In this case, the container means may itself be an inhalent, syringe, pipette, eye dropper, or other such like apparatus, from which the formulation may be applied to an infected area of the body, such as the lungs, injected into an animal, or even applied to and mixed with the other components of the kit. The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalent, syringe, pipette, forceps, measured spoon, eye dropper or any such medically approved delivery vehicle.

The following examples are presented in order to more fully illustrate the preferred embodiments of the invention. They should in no way be construed, however, as limiting the broad scope of the invention.

EXPERIMENTAL DETAILS SECTION

EXAMPLE 1

Construction of "Synthetic" Shear Stress Responsive Hybrid Promoter Constructs Based on Known SSREs

MATERIALS AND METHODS

Cone-Plate Shear Stress Apparatus

A cone-plate viscometer was used the design of which and the operating parameters have been described in details (26, 36). Shear stress is produced in the fluid contained between a stationary base plate and a rotating cone. By adjusting the cone angle, the viscosity of the medium and the cone rotational speed a wide broad of shear stress magnitudes (1–50 dynes/cm) and patterns (laminare, turbulent, disturbed-laminar and oscillatory) can be achieved. Confluent endothelial monolayers can be grown either on 11 mm in diameter twelve tissue culture coated coverslips to achieve multiple sampling under the same flow and medium conditions, or alternatively, on a 17 cm in diameter tissue culture coated coverslip for molecular biology procedures requiring high cell quantities. These two configurations enable promoter analysis (deletion and hybrid promoter systems) in transfected endothelial cells, as well as, electro mobility shift assays (FMSA), run-on experiments, RNA and protein extraction, and the results of which are described in the following sections.

Four positive SSREs were defined and tested, which include the PDGF/B SSRE which binds NFkB and NFAT, the PDGF/A SSRE which binds Sp1 and Egr1, the MCP-1 TRE which is binding site for fos and jun and the tissue factor SSRE, which is a binding site for Sp1. Interestingly, most of these promoters contain more than one of the described SSREs. PDGF-B promoter contains a binding site for fos and jun and an sp1 binding site in addition to the PDGF/B-SSRE. MCP-1 encodes for the PDGF/B-SSRE in addition to its TRE site. Tissue factor promoter contains NFkB, fos and jun binding sites, in addition to its spl/SSRE site. Shear stress responsiveness in vivo, is the result of the cooperative action of several SSREs in each promoter.

Figure 1:
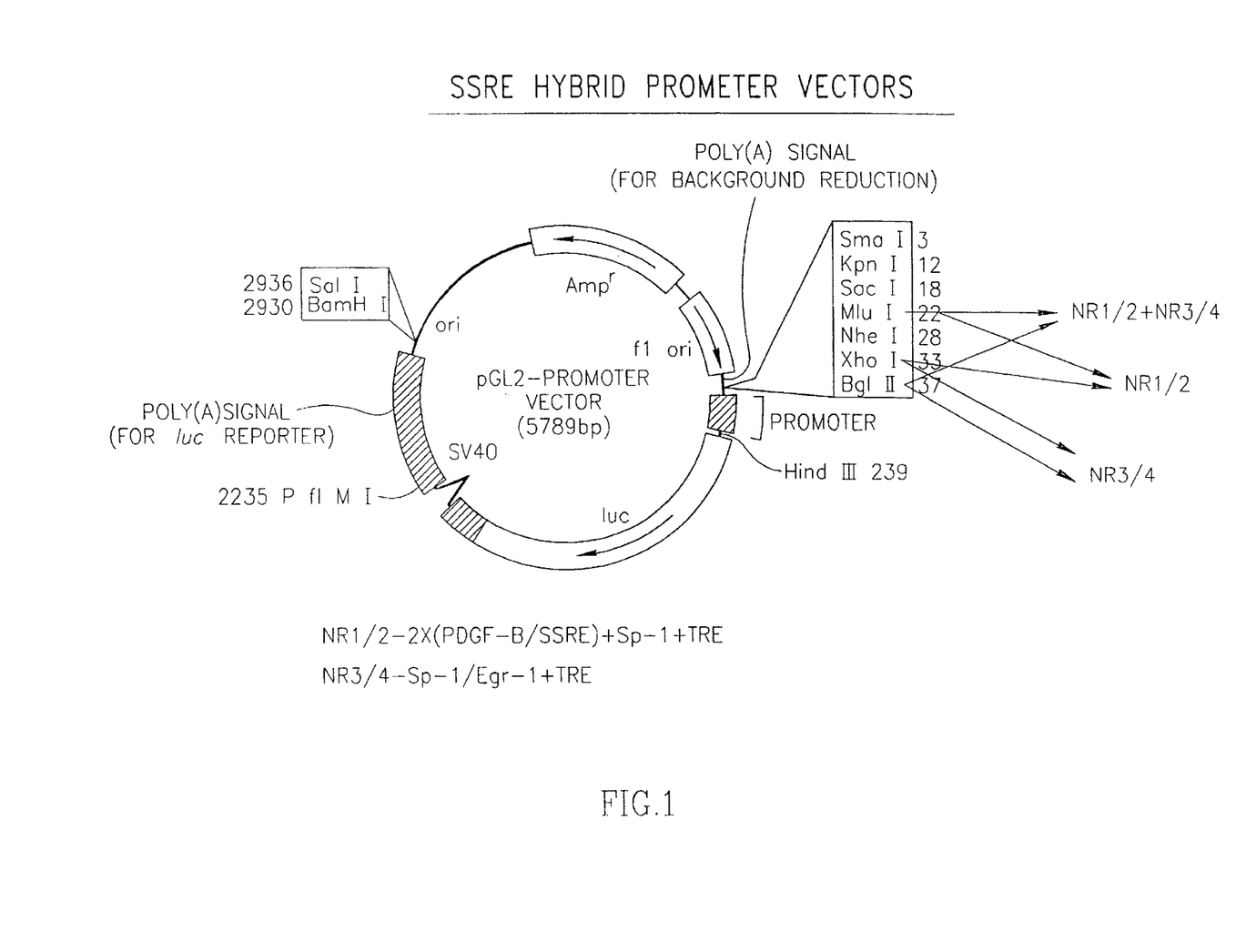
FIG. 1: Schematic of a SSRE hybrid promoter vector named pGL3-promoter vector (5789 bases) comprising one of the following: NR1/2+NR3/4; NR1/2; or NR3/4, promoter, poly(A) signal and/or a reporter gene. NR1/2 comprises nucleic acid sequences of two (2) PDGF-B SSRE, a Sp-1, and TRE, while NR3/4 comprises nucleic acid sequences of Sp-1/Egr-1 and TRE.

The vector pGL3-promoter, as shown in FIG. 1, containing the luciferase gen and the SV40 promoter (Promega, Madison, Wis., U.S.A) was used as a backbone to all of the described constructs.

Two oligonucleotides containing a combination of the known SSRE's were ligated into this backbone:

1. NR1/NR2-Luc:
   CGCCTGAGACCCCCGGGGCGGGGCGGAGA
   CCCCCTGACTCCCCACTCTGGGGGCCCCG
   CCCCGCCTCTGGGGGACTGAGGGAGCT (SEQ ID NO. 5)

This oligonucleotide contains the PDGF-B/SSRE sequence (GAGACCCCC (SEQ ID NO. 2)) twice, the Sp-1 binding site (GGGGCGGGGCG (SEQ ID NO. 4)) twice, the TRE site (TGACTCC (SEQ ID NO. 3)) twice and polylinkers to the restrictions enzymes MiuI and XhoI.

2. NR3/NR4-Luc:
   TCGAGGGGGGCGGGGGCGGGGGTGACTCCG
   AGACCCCCACCCCCCGCCCCCGCCCCCACT
   GTGGCTCTGGGGGTCTAG (SEQ ID NO. 6)

This oligonucleotide contains the Sp1/Egr1 sequence from the PDGF-A promoter (GGGGGCGGGGGCGGGGG (SEQ ID NO. 1)) twice, the PDGF-B/SSRE once (GAGACCCCC (SEQ ID NO. 2)), the TRE site (TGACTCC (SEQ ID NO. 3)) once, and polylinkers to the restriction enzymes XhoI and BglII. These constructs were ligated 5' to the SV40 promoter (both NR1/NR2 and NR3/NR4) to create the vectors 5' NR1/NR2-Luc and 5' NR3/NR4-Luc and also 3' to the luciferase gene (3' NR3/NR4-Luc) to test the positional effect of the SSREs. These constructs were used to transfect endothelial cells, and their expression was compared to already existing hybrid promoters containing each of the SSREs alone.

Transfection of Endothelial Cells

The efficiency of transfection of primary cells in general, and more specifically primary endothelial cell, is very low (1–5%). In order to detect significant differences in the inducibility of the various SSRE constructs, and since the inducibility of endothelial genes containing the SSREs is only about 3–5 folds, higher efficiency of transfection should be achieved.

To that end several commercially available transfection kits as well as a modified calcium phosphate method adapted by to suit endothelial cells were used. In these experiments three kits were used: The Tfx 20 and 50 (Promega, U.S.A). Fungene (Gibco-BRL, U.S.A) and Effectine (Qiagene, U.S.A). Endothelial cells from arterial and capillary origin (Bovine Aortic Endothelial cells-BAEC, and Bovine brain Capillary Edothelial cells-BBC0 were used for transfecion.

The efficiencies of transfection of BAEC with the various techniques were: Modified calcium phosphate (concentration of sodium hydrogen phosphate 1.4 mM), 22%, Effectine—19%, Fugene—15%, Tfx 20 —16%, and Tfx 50–20%. The efficiencies of transfection of BBC with the various methods were: Modified Calcium phosphatase: 8%, Effectine—15%, Fugene—15%, and Tfx 20—13% Tfx 50—7%.

Transfection of SSRE Constructs into Endothelial Cells

Endothelial cells were transfected in triplicate with three constructs: NR1/2 which contains the combination of all four SSREs, SSRE-Luc which contains a single copy of the PDGF-B/SSRE and the core plasmid PGL, and co-transfected with the Renilla luciferase vector. Two days after transfection the cells were transferred to a medium containing 5% calf serum and either incubated under static conditions or exposed to shear stress (10 dynes/cm$^2$, 4 hrs). The cells were extracted and the ratio luciferase/renilla luciferase was calculated. The induction of expression was calculated for the average ratio of the triplicates in shear stress versus. static experiments.

RESULTS

TABLE 1

The induction of SSRE-hybrid promoter vectors by shear stress.

| Name | Static | | | Shear stress | | | Induction |
|------|-----|------|-------|------|------|-------|-----------|
|      | Lac | Ral  | Ratio | Luc  | Ral  | Ratio |           |
| NR ½ | 64  | 3200 | 0.02  | 800  | 9900 | 0.08  | 4.38      |
|      | 71  | 5071 | 0.014 | 648  | 9900 | 0.065 |           |
|      | 83  | 5533 | 0.013 | 755  | 9900 | 0.076 |           |
| SSRE | 87  | 870  | 0.1   | 380  | 2225 | 0.17  | 1.75      |
|      | 103 | 687  | 0.15  | 1008 | 3900 | 0.25  |           |
|      | 31  | 282  | 0.11  | 148  | 4765 | 0.03  |           |
| PGL  | 75  | 1875 | 0.04  | 410  | 9900 | 0.04  | 0.9       |
|      | 48  | 960  | 0.05  | 368  | 9200 | 0.04  |           |
|      | 45  | 900  | 0.05  | 194  | 4850 | 0.04  |           |

TABLE II

The induction of SSRE-hybrid promoter vectors by shear stress

| Name | Static | | | Shear stress | | | Induction |
|------|-----|------|-------|--------|------|-------|-----------|
|      | Lac | Ral  | Ratio | Luc    | Ral  | Ratio |           |
| NR ½ | 25  | 3360 | 0.008 | 122.9  | 2776 | 0.044 | 5.1       |
|      | 21  | 2771 | 0.008 | 107.9  | 2365 | 0.041 |           |
|      | 33  | 2533 | 0.013 | 137.78 | 2821 | 0.049 |           |
| SSRE | 72  | 2870 | 0.025 | 124    | 2225 | 0.055 | 1.7       |
|      | 69  | 2287 | 0.03  | 156    | 3900 | 0.04  |           |
|      | 84  | 3282 | 0.025 | 172    | 4765 | 0.04  |           |

REFERENCES

1. Breier G., Damert A., Plate K H and Rissau W., 1997. Thrombosis and Haemostatis. 78:678–83.
2. Iruela-Arispe ML and Dvorak HF 1997. Thrombosis and Haemostatis 78:672–77.
3. Folkman J. and D'Amore P A 1996. Cell 87:1153–56.
4. Schapper W. and I to W D 1996. Circ. Res. 79–311.
5. Ware J. A. and Simons M. 1997. Nature Med. 3:1–58–64.
6. Hannahan D. 1997. Science 277:48–50.
7. Ferrara N., Carver-Moore K. Chen H., et al. 1996. Nature 380:439–42.
8. Shalaby F., Rossant J., Yamaguchi T. P., et al. 1995 Nature 376:62–66.
9. Fong G H, Rossant J., Gertenstein M., et al. 1995 Nature 376:66–70.
10. Dumont D. J. 1994. Genes Dev. 8:1897–1903.
11. Sato T N, Tzoawa Y1, Deutsch U., et al. 1995. Nature 376:70–74.
12. Suri C., Jones P F., Patan S. et al. 1996. Cell 87:1171–80.
13. Maisonpierre P C., Suri C., Jones P F., et al. 1997. Science 277:55–60.
14. Vikkula M., Boon L. M., Carraway M L., et al. 1996. Cell 87:1181–90.

15. Leveen P., Pekny M. Gebre-Medhim S., et al. 1994. Genese Dev. 8:1875–87.
16. Soriano P. 1994 Genes Dev. 8:1888–1892.
17. Dickson M C., Martin J S, Co U.S. Pat. No. ins FM et al. 1995. Development 121:1845–54.
18. Carmeliet P., Mackman N., Moons L., et al. 1996. Nature 383:73–75.
19. Rissau W. and Flame I. 1995 Ann Rev. Cell. Dev. Biol. 11:73–105.
20. Rissau W. 1997, Nature 386:671–675.
21. Stone J., Chan-Ling T., Peter J. et al., 1996. Invest. Opthalmol. Visual Sci. 37:290–99.
22. Alon t., Hemo In., Itin A., et al. 1995. Nature Med. 1:1024–28.
23. Frangos J A ed. 1993. In: Physical forces and the mammalian cell. Academics, San Diego, Calif.
24. Caro C G, Fitz-Geral J M, and Schorter R C. 1971. Proc. Natl. Acad. Sci. 177:109–159.
25. Ku DN, Giddens D P, Zarins C K and Galgov S 1985. Arteriosclerosis. 5:293–302.
26. Resnick N. and Gimbrone Jr. MA. 1995 FASEB J. 9:874–882.
27. Davies P F, Physiol. Rev. 1995
28. Resnick N., Collins T. Atkinson W. Bonthron D T, Dewey F C Jr. and Gimbrone M A Jr. 1993. Proc. Natl. Acad. Sci. U.S. Pat. No. A 90:4591–4595.
29. Kuwabara K. et al. 1995. Proc. Natl. Acad. Sci. U.S. Pat. No. A 92:4606–610.
30. Shweiki D., Itin A., Soffer D. and Keshet E. 1992. Nature 359:843–45.
31. Tuder R M., Flook B E, and Voelkel N F 1995 J. Clin. Invest. 95:1798–1807.
32. Levy A P., Levy N S Loscalzo J. et al. 1995. Circ. Res. 76:756–766.
33. Schaper W., and Schaper J. 1993. In:Collateral Circulation: Heart, Brain, kidney, limb, London UK, Kluwer Academic Publishers.
34. Yang H T., Ogilvia R W., and Terjung R L 1994. Circ. Res. 74:235–43.
35. Ziche M. Morbidell L. Choudhuri R. et al. 1997. J. Clin. Invest. 99:2625–34.
36. BU.S. Pat. No. solari SR, Dewey C F Jr., and Gimbrone M A Jr. 1982. Rev. Sci. Instrum 53:1851–1854.

What is claimed is:

1. A recombinant vector comprising a multiple number of nucleic acids of Shear Stress Response Elements (SSRE), wherein the Shear Stress Response Elements are selected from the group consisting of Shear Stress Response Element PDGF-A, Shear Stress Response Element PDGF-B, Shear Stress Response Element SP1, and Shear Stress Response Element TRE.

2. The vector of claim 1, wherein the Shear Stress Response Elements (SSRE) are from promoters of growth factors, thrombogenic factors or angiogenic genes.

3. The vector of claim 1, wherein the nucleic acids are in a sense or anti-sense orientation.

4. The vector of claim 3, wherein the nucleic acid of the PDGF-A is set forth in SEQ ID NO: 1.

5. The vector of claim 1, wherein the Shear Stress Response Element are Shear Stress Response Element PDGF-B, Shear Stress Response Element PDGF-B, Shear Stress Response Element SP1, and Shear Stress Response Element TRE.

6. The vector of claim 3, wherein the nucleic acid of the PDGF-B is set forth in SEQ ID NO: 2.

7. The vector of claim 1, wherein the Shear Stress Response Element are Shear Stress Response Element PDGF-A, Shear Stress Response Element PDGF-B, Shear Stress Response Element TRE.

8. The vector of claim 3, wherein the nucleic acid of the SP-1 is set forth in SEQ ID NO: 3.

9. The vector of claim 1, wherein the Shear Stress Response Elements are one or more, or a combination of Shear Stress Response Element PDGF-A, Shear Stress Response Element PDGF-B, Shear Stress Response Element TRE, or Shear Stress Response Element SP1.

10. The vector of claim 9, wherein the nucleic acid is set forth in SEQ ID NO: 5.

11. The vector of claim 9, wherein the nucleic acid is set forth in SEQ ID NO: 6.

12. The vector of claim 1, wherein the vector is a plasmid, YAC, BAC, adenovirus, adeno-associated virus, rhabdovirus, herpes simplex virus, swinepox virus, or vaccinia virus.

13. The vector of claim 1, further comprising a nucleic acid encoding NFKB, MCP-1, NFAT, sp1/Egr 1, c-fos, c-jun, c-myc, PDGF A, PDGF B, TM, b-FGF, TGF, eNOS, HO-1, cu/Zn SOD, VCAM-1, I-CAM, Connecxin 43, PGI synthase, smad 6, smad 7, TGF-β, HB-EG CNP, COX-2, thrombospondin, ICAM, ELAM-1, cyclooxygenase, angiopeitin 1, tenscin, angiopeitin 2, laminin B1, IL-1, I1-2, I1-3, I1-4, I1-4, IL-6, I1-7, I1-8, I1-9, I1-10, I1-11, I1-12, ACE or VEGF.

14. The vector of claim 13, wherein the nucleic acid is under the control of a promoter.

15. The vector of claim 14, wherein the promoter is SV40, Rous Sarcoma Virus, Cytomegalovirus, or Human Cytomegalovirus.

16. The vector of claim 1, further comprising a reporter gene, a selection marker, a transmembrane protein, an enzyme, a secreted factor, or a gene coding for any protein with therapeutic function.

17. The vector of claim 16, wherein the reporter gene is luciferase, β-galactosidase, or β-lacatamase, MHC I or II sub-types, or a receptor for growth factor or cell adhesion.

18. A host cell which comprises the vector of claim 14.

19. A composition comprising the vector of claim 1 and a suitable diluent or carrier.

* * * * *